United States Patent
Price

(10) Patent No.: US 7,595,204 B2
(45) Date of Patent: Sep. 29, 2009

(54) METHODS AND SYSTEMS FOR DETERMINING TRAPPED CHARGE DENSITY IN FILMS

(75) Inventor: James Martin Price, Austin, TX (US)

(73) Assignee: Sematech, Inc., Austin, TX (US)

( * ) Notice: Subject to any disclaimer, the term of this patent is extended or adjusted under 35 U.S.C. 154(b) by 345 days.

(21) Appl. No.: 11/464,884

(22) Filed: Aug. 16, 2006

(65) Prior Publication Data

US 2007/0213954 A1 Sep. 13, 2007

Related U.S. Application Data

(60) Provisional application No. 60/780,171, filed on Mar. 7, 2006.

(51) Int. Cl.
*H01L 21/66* (2006.01)
(52) U.S. Cl. ........................................ 438/14
(58) Field of Classification Search ............... None
See application file for complete search history.

(56) References Cited

U.S. PATENT DOCUMENTS

| 5,660,895 | A | * | 8/1997 | Lee et al. ............... | 427/579 |
| 2006/0065919 | A1 | * | 3/2006 | Fujiwara ............... | 257/315 |

FOREIGN PATENT DOCUMENTS

WO    WO 98/28606    7/1998

OTHER PUBLICATIONS

"An Efficient Analytical model for Calculating Trapped Charge in Amorphous Silicon"; Yao-Tsung Tsai, Kuo-Don Hong, Yin-Lun Yuan: IEEE Transactions on Computer Aided Design of Integrated Circuits and Systems: vol. 13, No. 6, Jun. 1994.*
Aspnes et. al., "Resonant nonlinear optical susceptibility: electoreflectance in the low-field limit," *Phys. Rev. B*, 5:4022, 1972.
Aspnes, "Third-derivative modulation spectroscopy with low-field electroreflectance," *Surface Science*, 37:418, 1973.
Callaway, "Optical absorption in an electric field," *Phys. Rev.*, 130:549, 1963.
Carriles et. al., "Second-harmonic generation from $Si/SiO_2/Hf_{(1-x)}Si_xO_2$ structures," *Appl. Phys. Lett.*, 88:161120, 2006.

(Continued)

*Primary Examiner*—Charles D. Garber
*Assistant Examiner*—Andre' C Stevenson
(74) *Attorney, Agent, or Firm*—Fulbright & Jaworski L.L.P.

(57) ABSTRACT

Methods and systems for determining a charge trap density between a semiconductor material and a dielectric material are disclosed. In one respect, spectroscopic data of the semiconductor material may be determined and used to determine a change in dielectric function. A line shape fit of the change in the dielectric function may be applied using derivative function form. The amplitude of the line shape fit may be determined and used to determine an electric field of a space charge region of the semiconductor material. By applying Poisson's equations, the scalar potential due to the electric field in the space charge region may be determined. Subsequently, using the scalar potential the charge trap density may be determined.

17 Claims, 8 Drawing Sheets

OTHER PUBLICATIONS

Carriles et. al., "Optical characterization of process-dependent charging in hafnium oxide structures," *Journ. Vac. Sci. Technol. B*, 24:2160 (2006).

Fulton et. al., "Process-dependent band structure changes of transition-metal (Ti,Zr,Hf) oxides on Si (100)," *Appl. Phys. Lett.*, 84:580, 2004.

Fulton et. al., "Interface instabilities and electronic properties of $ZrO_2$ on silicon (100)," *Journ. Appl. Phys.*, 96:2665, 2004.

Gavartin et. al., "The role of nitrogen-related defects in high-$k$ dielectric oxides: Density-functional studies," *Journ. Appl. Phys.*, 97:053704, 2005.

Heh et. al., "Spatial distributions of trapping centers in $HfO_2$/Si $O_2$ gate stacks," *Appl. Phys. Lett.*, 88:152907, 2006.

Li et. al., "High permittivity quaternary metal ($HfTaTiO_x$) oxide layer as an alternative high-κ gate dielectric," *Appl. Phys. Lett.*, 89:103523-1-103523-3, 2006.

Kang et. al., "Transient bicarrier response in high-κ dielectrics and its impact on transient charge effects in high-κ complementary metal oxide semiconductor devices," *Appl. Phys. Lett.*, 88:162905, 2006.

Lim et. al., "Temperature dependent defect formation and charging in hafnium oxides in silicates," *Journ. Vac. Sci. Technol. B*, 23:201, 2005.

Malin et. al., "Generalized ellipsometric method for the determination of all the optical constants of the system: Optically absorbing film on an absorbing substrate," *Surface Science*, 56:49-63, 1976.

Tharmalingam, "Optical absorption in the presence of a uniform field," *Phys. Rev.*, 130:2204, 1963.

Wilk et. al., "High-κ gate dielctrics: Current status and materials properties considerations," *Journal Appl. Phys.*, 89:5243, 2001.

Xiong et. al., "Defect energy levels in $HfO_2$ high-dielectric-constant gate oxide," *Appl. Phys. Lett.*, 87:183505-1-183505-3, 2005.

Zaghoul et. al., "Inversion of the nonlinear equations of reflection ellipsometry on film-substrate systems," *Surface Science*, 56:87-96, 1976.

PCT/US2007/063406 Search Report mailed May 30, 2007.

Bell et al., "Systematic differences among nominal reference dielectric function spectra for crystalline Si as determined by spectroscopic ellipsometry," *Thin Solid Films*, 313:161-166, 1998.

Price et al., "Spectroscopic ellipsometry characterization of Hf(x)Si(x)O(z) films using the Cody-Lorentz parameterized model," *Applied Physics Letters*, 85:1701-1703, 2004.

Takeuchi et al., "Obervation of bulk HfO(2) defects by spectroscopic ellipsometry," *J. Vac. Sci. Technol.*, 22:1337-1341, 2004.

Zhu et al., "Charge trapping in ultrathin hafnium oxide," *Ieee Electron Device Letters*, 23:597-599, 2002.

PCT/US2007/063406 Search Report mailed May 30, 2007.

Bell et at, "Systematic differences among nominal reference dielectric function spectra for crystalline Si as determined by spectroscopic ellipsometry," *Thin Solid Films*, 313:161-166, 1998.

Price et al., "Spectroscopic ellipsometry characterization of Hf(x)Si(x)O(z) films using the Cody-Lorentz parameterized model," *Applied Physics Letters*, 85:1701-1703, 2004.

Takeuchi et al., "Obervation of bulk HfO(2) defects by spectroscopic ellipsometry," *J. Vac. Set Technol.*, 22:1337-1341, 2004.

Zhu et al., "Charge trapping in ultrathin hafnium oxide," *Ieee Electron Device Letters*, 23:597-599, 2002.

\* cited by examiner

METHODS AND SYSTEMS FOR DETERMINING TRAPPED CHARGE DENSITY IN FILMS

This application claims priority to, and incorporates by reference, U.S. Provisional Patent Application Ser. No. 60/780,171 which was filed Mar. 7, 2006.

BACKGROUND OF THE INVENTION

1. Field of the Invention

The present invention relates generally to semiconductor fabrication. More particularly, the present invention involves detecting trapped charge densities in films, such as dielectric films.

2. Description of Related Art

As device sizes continue to be reduced and a there is a demand for higher performance and faster products, scaling of the traditional gate oxide layer has gone below 2 nanometers. As a result, leakage currents due to tunneling have increased, thereby inhibiting the performance of devices. Current integrated circuit (IC) manufacturing processes have implemented the replacement of traditional gate oxide layer, generally silicon dioxide ($SiO_2$) with high-k dielectrics to maintain a low gate leakage current density.

However, poor transistor drive current due to degraded field effect carrier mobility is a major issue with high-k dielectrics. This affect counters one of the top priorities of successful IC scaling goals which include an improvement of mobility. The observed degradation of mobility has been primarily attributed to localized charge traps at the interface between a crystalline substrate and a dielectric material. For example, Hafnium based dielectrics have been studied extensively, both theoretically and experimentally, to determine both the density of these defects and the energy at which they lie within the band gap of the dielectric. It has been found that for $HfO_2$ with a band gap of approximately 6.0 electron volts (eV), the charge traps are oxygen vacancies and interstitials that reside about 0.3-0.5 eV below the band gap and have a density of about $1 \times 10^{11}$ to about $1 \times 10^{13}$ $cm^{-2}$.

Much effort has been put forth to decrease the amount of these oxygen vacancies by introducing other elements into the film (i.e. hafnium silicates) or with process optimization (e.g., high temperature anneals which fill the vacancies with the anneal ambient). However, during the manufacturing process, there is no method available to determine the extent of charge trapping. It is therefore necessary for an in-line metrology technique to be available that can detect gate dielectrics with a high density of charge traps before transistor processing is complete.

Unfortunately, current techniques to determine the extent of charge traps introduced into the dielectric film include electric capacitance-voltage (CV) measurements and current-voltage (IV) measurements, which are offline techniques. Observation of hysteresis in the capacitance versus the voltage curves may indicate charge trapping. This technique is an off-line, destructive technique (e.g., requiring sacrificial wafers for processing), and in many cases (especially high-k development), has failed to reflect the reality of the complex trapping structures in the dielectrics due to subsequent processing conditions such as high temperature anneal, gate electrode metal deposition, and the like.

Another technique, modulation spectroscopy, which includes photo reflectance, electro reflectance, piezo reflectance, thermo reflectance, and the like, may be used to characterize charge trapping. Generally, a reflectivity induced by a pertubative mechanism (e.g., laser, electric field, stress, temperature, and the like) applied to the material is measured. In particular, modulation spectroscopy measures the normalized change in reflectivity described by $$\frac{\Delta R}{R} = \alpha \Delta \varepsilon_1 + \beta \Delta \varepsilon_2,$$

where $$\alpha = \frac{\partial Ln|R|}{\partial \varepsilon_1} \text{ and } \beta = \frac{\partial Ln|R|}{\partial \varepsilon_2}.$$

The modulation spectroscopy techniques provides some benefits by accentuating the discontinuities in the real ($\in_1$) and imaginary ($\in_2$) part of the dielectric function at the various critical points in the band structure. These features are enhanced by measuring the differential of the critical points ($\Delta\in$), while baseline features associated with the film thickness, roughness, and other $2^{nd}$ order effects are suppressed.

However, modulation techniques are unable to accurately measure the charge trap induced changes in the substrate dielectric function because of the functional dependents of Seraphin coefficients ($\alpha$ and $\beta$) that act to scale the changes in the real or imaginary part of the dielectric function. For example, for a multilayer system (e.g., gate dielectric layer and substrate layer), the reflectivity R, is a function of film thickness, dielectric function of each film, and incident angle. Therefore, the Seraphin coefficient that multiplies the change in the dielectric function will be different for different films and thicknesses and would affect the amplitude of the change in the dielectric function for different thicknesses, compositions, etc. Thus, it would be difficult to extract information about the charge trap induced electric field without knowing exactly the thickness of the film, dielectric function of the film, and incident angle of each layer because modulations techniques do not provide thickness of films, dielectric function of film, and incident angles.

Any shortcoming mentioned above is not intended to be exhaustive, but rather is among many that tends to impair the effectiveness of previously known techniques for identifying charge traps in dielectric material; however, shortcomings mentioned here are sufficient to demonstrate that the methodologies appearing in the art have not been satisfactory and that a significant need exists for the techniques described and claimed in this disclosure.

SUMMARY OF THE INVENTION

The present disclosure provides a linear optical technique, that is in-line (i.e., does not interfere with the full production of a wafer) and non-destructive (i.e., does not require sacrificial wafers), for identifying charge trap densities present in gate dielectric materials. The techniques of the present disclosure may use an electric field induced across a space charge region of a crystalline structure due to the charge traps at the interface between a crystalline substrate and a dielectric material. This electric field has an immediate impact on the crystalline absorption edge. This field induced change in the absorption edge is analogous to modulation and non-linear spectroscopy techniques which deliberately modulate the electric field in the space charge region by an external mechanism (e.g. a pump laser). By contrast, this new linear method identifies the changes in the silicon absorption edge induced by the built in electric field. The present technique further provides increased accuracy in determining $\Delta\in$ of Eq. 1 by about three to five orders of magnitude greater than conventional modulation techniques.

In one respect, a method for determining the charge trap density of an interface between a semiconductor material and a dielectric oxide layer is provided. The method may include obtaining spectroscopic data (e.g., Psi, Delta, and reflectivity) of the semiconductor material and using the spectroscopic data to determine a perturbed substrate dielectric function. The perturbed substrate dielectric function may subsequently be used to determine an electric field.

The method may also provide performing a line shape fit of the change in the dielectric function using a derivative functional form, such as, but not limited to, a third derivative functional form Lorentzian line shape fit. Next, an amplitude of the line shape may be determined. The amplitude may be used to determine an electric field of a space charge region of the semiconductor material. The scalar potential may be determined from the derived electric field, and used to determine a charge trap density of an interface between the semiconductor material and the dielectric oxide layer from the scalar potential.

The present disclosure may also provide for calculating a perturbed substrate dielectric function. In one respect, the perturbed substrate dielectric function may be determined spectroscopic data from a semiconductor may be obtained.

In other respects, the present disclosure may determine an electric field from the perturbed dielectric function. Subsequently, a charge trap density between a semiconductor material and a dielectric oxide layer may be determined from the electric field induced charge.

The present disclosure may also provide a system comprising, amongst other things, a light source for illuminating a semiconductor material including a dielectric material, a detector coupled to the light source for detecting light from the semiconductor material, and a process coupled to the detector.

In some respect, the process may be configured for obtaining spectroscopic data corresponding to the semiconductor material. From the spectroscopic data, a perturbed substrate dielectric function may be determined. The processor may use the perturbed substrate dielectric function and determine, amongst other things, a change in the dielectric function, a line shape fit dielectric function, an amplitude of the line shape fit, and subsequently an electric field of a space charge region of the semiconductor material from, for example, the amplitude. From the electric field, and in some embodiments, a scalar potential of the electric field, a charge trap density of an interface between the semiconductor material and the dielectric oxide layer may be determined.

An "interfacial layer region" as defined and used in this disclosure may be defined as a 1 to a 1.5 nanometer area between a substrate and dielectric layer where mixing and/or inter-diffusion may occur.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one-non and in one non-limiting embodiment the substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The figures are examples only. They do not limit the scope of the invention.

DESCRIPTION OF ILLUSTRATIVE EMBODIMENTS

The disclosure and the various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

The disclosure provides for using a perturbation theory (e.g., a first order time independent perturbation theory and/or a third order time dependent perturbation theory) to determine theoretical relationship relating the changes due to an internal electric field across the silicon space charge region. From the derived electric field and knowledge obtained from conventional spectroscopic ellipsometry measurements to determine the thickness, the potential across the interface may be found. For example, using Poisson's equation and knowledge of the potential, the space charge density may then be determined.

In one embodiment, if a gate dielectric material deposited on a semiconductor substrate has a certain amount of defects related to charge traps at the interface, then electrons tunneling from the crystalline substrate may reside in these trapping centers. This subsequently creates a uniform electric field transverse to the surface of the sample and distributed substantially homogenously across a space charge region.

Figure 1:
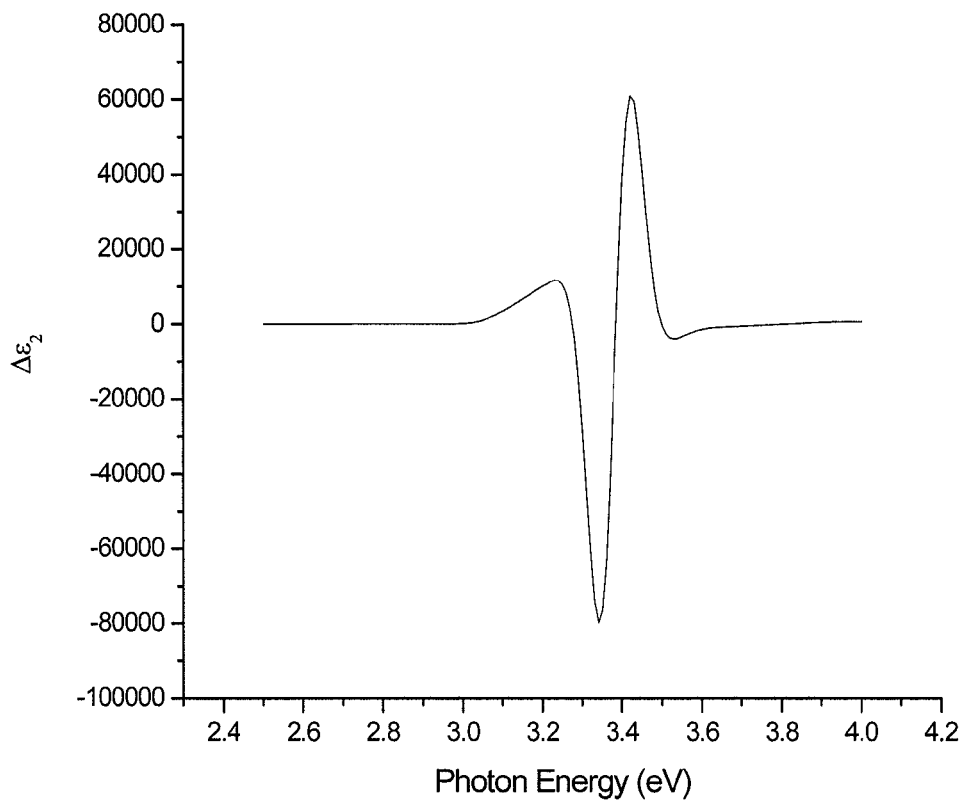
FIG. 1 is a graph showing a change in the imaginary part of the dielectric function at the fundamental absorption edge in the presence of a uniform electric field, in accordance with embodiments of this disclosure.

It is well known that a uniform electric field applied to a crystalline semiconductor material causes a change in the dielectric function of the material. Specifically, for low electric fields (where the electric field is less than the energy associated with the lifetime broadening of the electron), the change in the dielectric function near the fundamental absorption edge may be expressed as:

$$\Delta \varepsilon \propto E^2 \frac{\partial^3 ((\hbar \omega)^2 \varepsilon)}{\partial (\hbar \omega)^3} \qquad \text{Eq. 1}$$

where E is the electric field, $\hbar$ is Planck's constant, $\omega$ is the angular frequency associated with the incident light (photon), and $\in$ is the unperturbed dielectric function Referring to FIG. 1 and Eq. 1, the change in the dielectric function may take the shape of the third derivative of the un-perturbed dielectric function with an electric field (E) affecting the amplitude. This phenomenon is well known and has been extensively studied by linear modulation techniques such as electro-reflectance, photo-reflectance, and photo-ellipsometry.

In one embodiment, conventional spectroscopic ellipsometry (SE) may be used to determine built-in induced electric field caused by the charge traps. This is contrary to current conventional techniques which use an applied external electric field to study the change in the dielectric function of the material. By measuring the substrate dielectric function, and subtracting the unperturbed dielectric function, the relation of Eq. 1 may be determined. Next, an amplitude of the third derivative functional form of the data, to determine the electric field may be determined. Multiplying the electric field by the thickness of the interfacial region, may yield a scalar potential across the substrate space charge region. Finally, using Poisson's equation:

$$\rho = \frac{V \varepsilon_0}{2\pi d^2}, \qquad \text{Eq. 2}$$

where $\rho$ is the charge density, V is the electrostatic potential, $\in_0$ is the dielectric constant, and d is the thickness of the interfacial region, one may obtain the charge density. For more complicated geometries or charge distributions (associated with different device structures), one may solve the general form of Poisson's equation shown below to determine the charge density:

$$\frac{d^2 V}{dz^2} = \frac{-4\pi\rho}{\varepsilon_0}. \qquad \text{Eq. 3}$$

By first identifying the electric field, the charge trap density may be determined. Each of the above steps is described in more detail below.

In one respect, a method for determining charge trap density is provided. The method may be applied using several variations of a SE tool and/or sample of interest. Examples of such samples may include any crystalline semiconductor material such as, for example, silicon, germanium, gallium arsenide (GaAs), gallium nitride (GaN), indium phosphide (InP), zinc sulfide (ZnS), silicon germanium (SiGe), Silicon-on-Insulator (SOI), silicon germanium-on-Insulator (GeOI), or any other suitable materials. Other crystalline semiconductor materials may also be acceptable. The sample may include a dielectric oxide deposited on top with charge traps that create an electric field across the space charge region of the substrate. The dielectric oxide may include, for example, silicon dioxide, silicon oxy-nitride, hafnium dioxide, hafnium silicates, hafnium silicon nitrides, zirconium oxides, zirconium silicates, zirconium silicon nitrides, and the like.

In one non-limiting example, an $HfO_2$ film, having a thickness of about 3 nanometer was deposited on a <100> silicon substrate. All spectroscopic data was taken on a J. A. Woollam spectroscopic ellipsometer over the energy range of about 0.75 eV to 5 eV by 0.01 eV increments, where a change in the dielectric function occurs. The angles of the measurement ranged from 70-78°, incrementing by 4 degree increments. One of ordinary skill in the art can understand that angle of measurement may vary from about 0° to about 90°, with any degree of incrementation.

Figure 2:
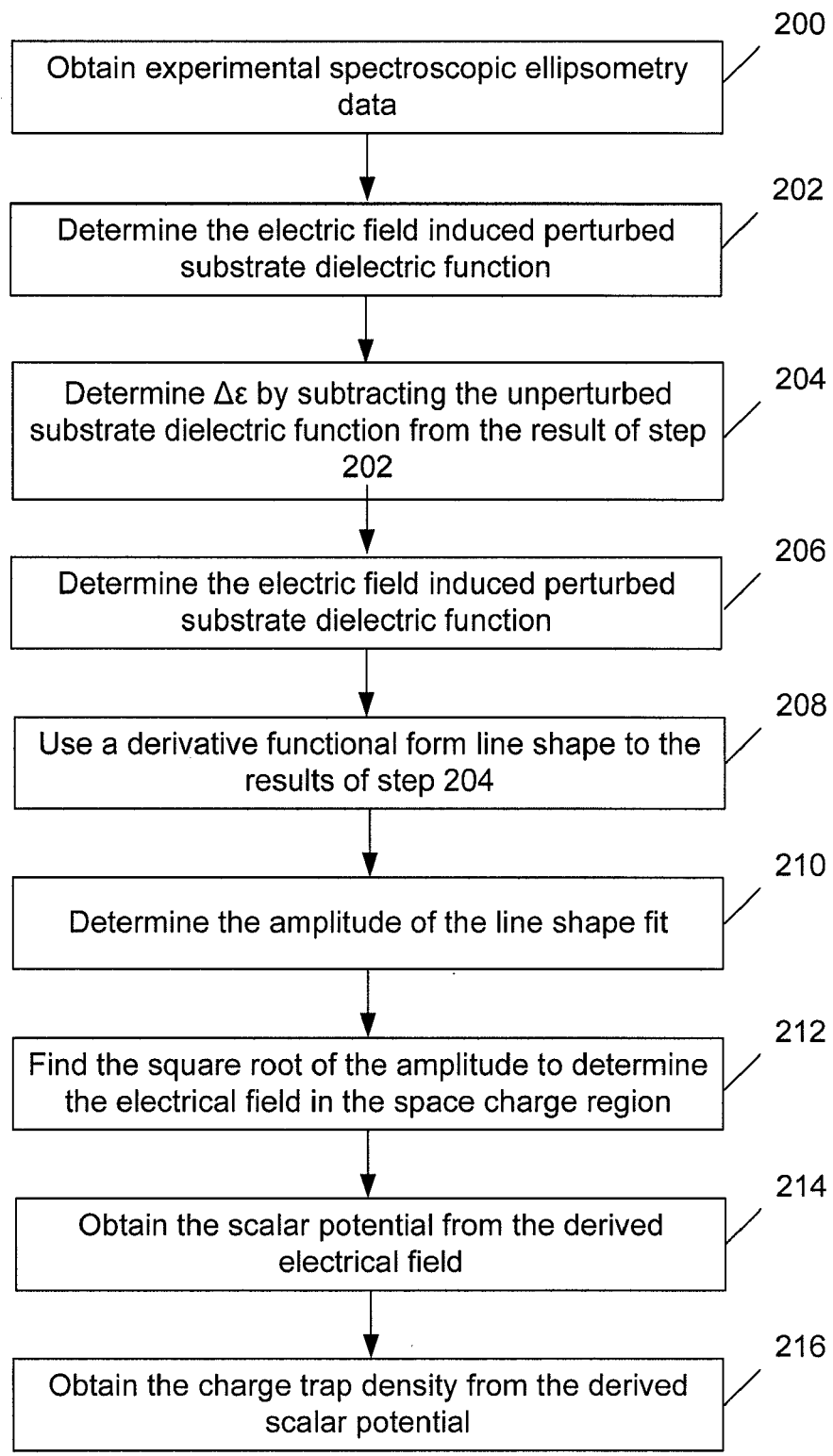
FIG. 2 is a flowchart of a method to determine charge trap density, in accordance with embodiments of this disclosure.

Referring to FIG. 2, one embodiment of a method in accordance with the present disclosure is presented. In step 200, a spectroscopic ellipsometer is used to acquire experimental data (e.g., Psi data 300 and Del data 302, FIG. 3) from a sample. In one embodiment, the system shown in FIG. 4 may be used to obtain data. Referring to FIG. 4, a spectroscopic ellipsometer is shown, where the spectroscopic ellipsometer may include, without limitation, light source 100, detector 408 and optional components polarizing lens 402 and analyzer 406. In some respect, the spectroscopic ellipsometer may be coupled to processor 410. Light source 400 may include, without limitation, lasers, ultraviolet (UV), visible light source and the like, and which may be positioned at an angle of incidence, may include multi-wavelengths (spectroscopic) and may be used to illuminate sample 404. Sample 404 may be a substrate comprising a dielectric oxide layer.

In one embodiment, the beam of light from light source 400 may be optionally polarized using techniques known in the art. For example, polarizing lens 402 may be provided and an incident polarized photon beam may be provided to sample 404. Alternatively, the light beam from light source 400 may be applied directly to sample 404.

The light beam from light source 400 may be reflected from sample 404 and may be directed towards analyzer 406. In one embodiment, analyzer element 406 may be used for polarization based techniques know in the art. Alternatively, the beam reflected off of sample 404 may be directly provided to detector 408. Detector 408 may generate data corresponding to techniques, such as, but not limited to, spectroscopic ellipsometry, reflectometry, and/or a combination of the above. The data may be sent to processor 410. Processor 410 may include any computer-readable media known in the art. For example, the computer-readable media may be embodied internally or externally on a hard drive, ASIC, CD drive, DVD drive, USB drive, tape drive, floppy drive, network drive, flash, or the like. Processor 410 may be any computing device capable of executing instructions for receiving the data from the detector and amongst other functions, may implement the steps shown in FIG. 2. In one embodiment, processor 410 is a personal computer (e.g., a typical desktop or laptop computer operated by a user). In another embodiment, processor may be a personal digital assistant (PDA) or other handheld computing device.

In some embodiments, processor 410 may be a networked device and may constitute a terminal device running software from a remote server, wired or wirelessly. Input from a user, detector 408, or other system components, may be gathered through one or more known techniques such as a keyboard and/or mouse. Output, if necessary, may be achieved through one or more known techniques such as an output file, printer, facsimile, e-mail, web-posting, or the like. Storage may be achieved internally and/or externally and may include, for example, a hard drive, CD drive, DVD drive, USB drive, tape drive, floppy drive, network drive, flash, or the like. Processor 410 may use any type of monitor or screen known in the art, for displaying information, such as but not limited to, figures similar to FIGS. 3 and 5-8. For example, a cathode ray tube (CRT) or liquid crystal display (LCD) can be used. One or more display panels may also constitute a display. In other embodiments, a traditional display may not be required, and processor 410 may operate through appropriate voice and/or key commands.

The spectroscopic ellipsometer data may be obtained using a single angle of incidence, or multiple angles of incidences. The spectroscopic ellipsometer may use a broadband or visible light source, as well as a laser, to obtain spectroscopic data in the region of interest. Alternatively, other electromagnetic radiation sources providing an ultraviolet wavelength, a visible wavelength, an infrared wavelength, or a combination thereof may be used.

In one embodiment, a spectroscopic data region of interest may coincide with the crystalline semiconductor substrates direct absorption edge (e.g., for silicon, the direct absorption edge may be at about 3.38 eV). It is noted that for different semiconductor substrates, the direct absorption edge may vary. For example, referring to Table 1, a list of the direct absorption edge values for various substrates is provided. One of ordinary skill in the art may readily determine for the direct absorption edge using conventional techniques known in the art.

TABLE 1

List of the Direct Absorption Edge Values for Different Substrates

| SUBSTRATE | E1 ENERGY (eV) |
|---|---|
| Si | 3.395 |
| Ge | 2.108 |
| SiGe (Ge = 5%) | 2.18 |
| SiGe (Ge = 10%) | 2.22 |
| SiGe (Ge = 15%) | 2.27 |
| SiGe (Ge = 20%) | 2.34 |
| GaAs | 2.9 |
| GaN | 7 |
| InP | 3.15 |

Figure 3:
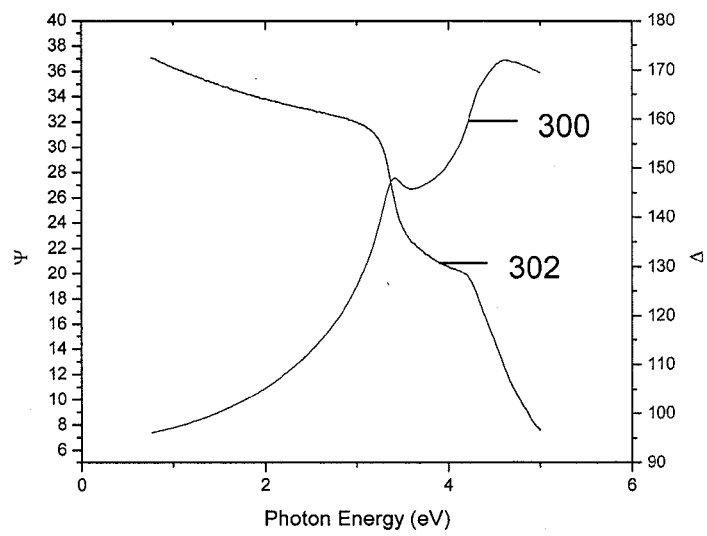
FIG. 3 is data obtained from a spectroscopic ellipsometer showing change in amplitude and phase of the reflected polarization, respectively, in accordance with embodiments of this disclosure.
Figure 4:
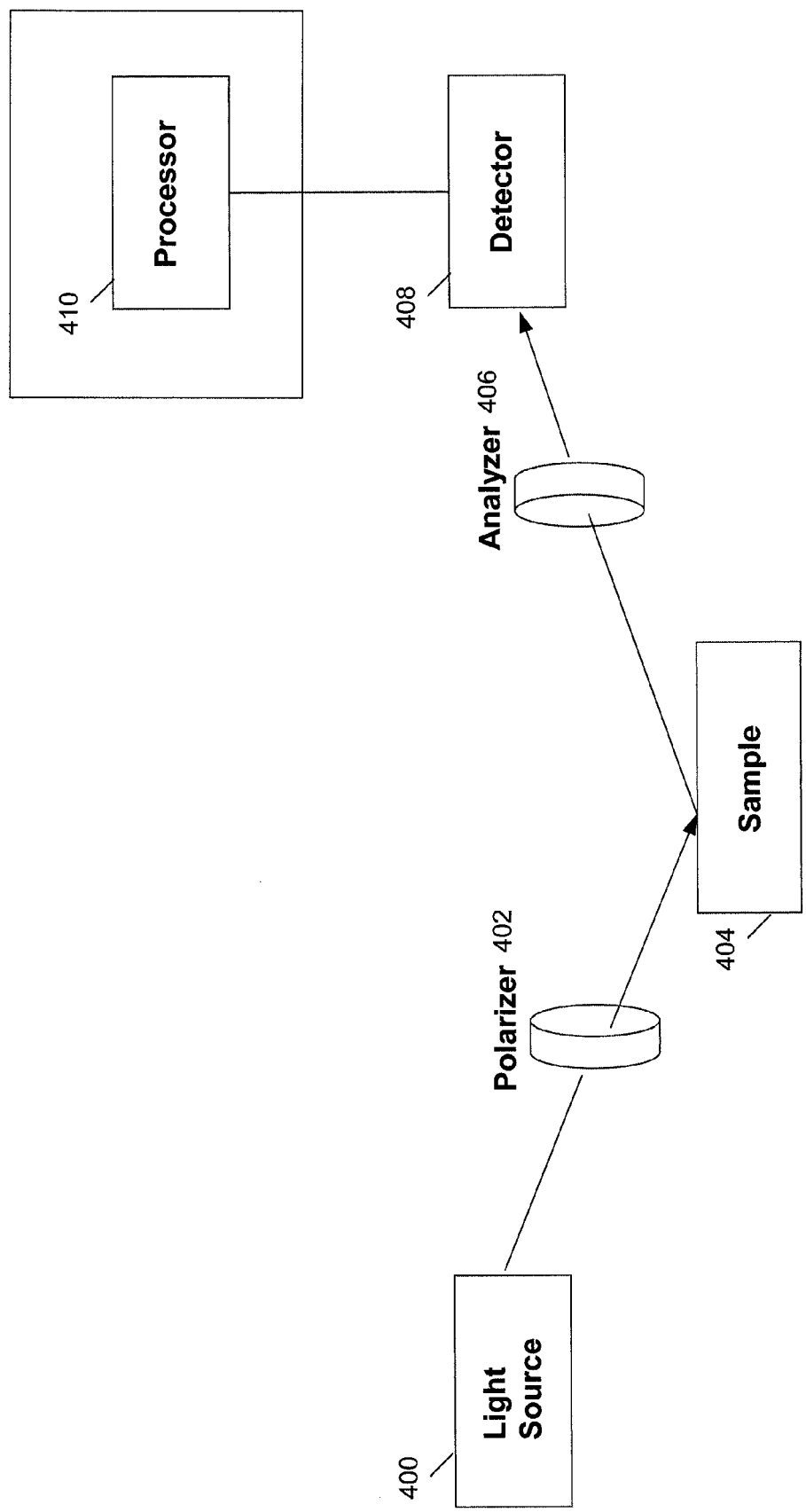
FIG. 4 is a system, in accordance with embodiments of this disclosure.
Figure 5:
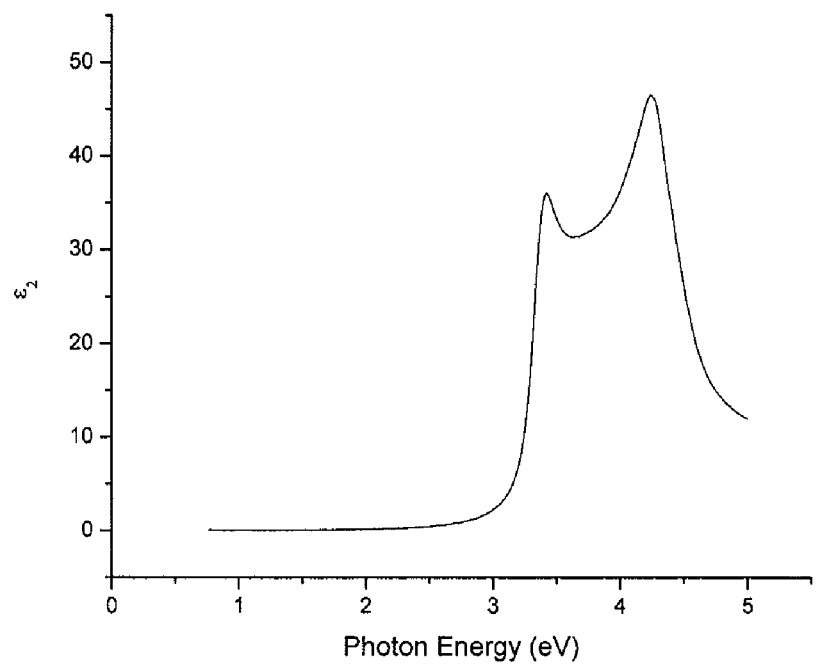
FIG. 5 is a graph showing the imaginary part of the dielectric function for a silicon substrate in the presence of a uniform electric field caused by charge traps residing at the interface of the gate dielectric material, in accordance with embodiments of this disclosure.

Referring again to FIG. 2, in step 202, the perturbed substrate dielectric function may be determined, using for example the SE data obtained in FIGS. 3 and 4. (See, e.g., FIG. 5). This may be accomplished in multiple ways. In one embodiment, the perturbed substrate dielectric function may be solved using the methods known in the art. (See, e.g., Malin et al., 1976; Zaghloul et al, 1976).

Alternatively, the thickness and index of refraction of the dielectric film may be determined for wavelengths below the fundamental absorption edge of the substrate. For this spectroscopic range (corresponding to that below the fundamental absorption edge of the substrate), the substrate dielectric function is not expected to change due to the charge trap induced electric field. Therefore, using an un-perturbed substrate dielectric function, one may accurately obtain the thickness and index of refraction of the dielectric film using a simple Cauchy optical model for the dielectric film. For the Cauchy model, the index of refraction follows the typical inverse power law according to:

$$n(\lambda) = A + \frac{B}{\lambda^2} + \frac{C}{\lambda^4}. \qquad \text{Eq. 4}$$

Here, n is the index of refraction, $\lambda$ is the wavelength of light, and A, B, and C are fitting constant coefficients. Once the fitting coefficients are determined for photon energies below the fundamental absorption edge, the index of refraction can be interpolated for higher photon energies using the Cauchy formula (Eq. 4)

Once the thickness and index of refraction is determined, the equations of ellipsometry may be solved for the optical properties of the substrate over the whole spectroscopic range, which may correspond to a range of wavelengths for which the data was obtained. In one embodiment, the spectroscopic range is about 0.75 to 5.0 eV.

Figure 6:
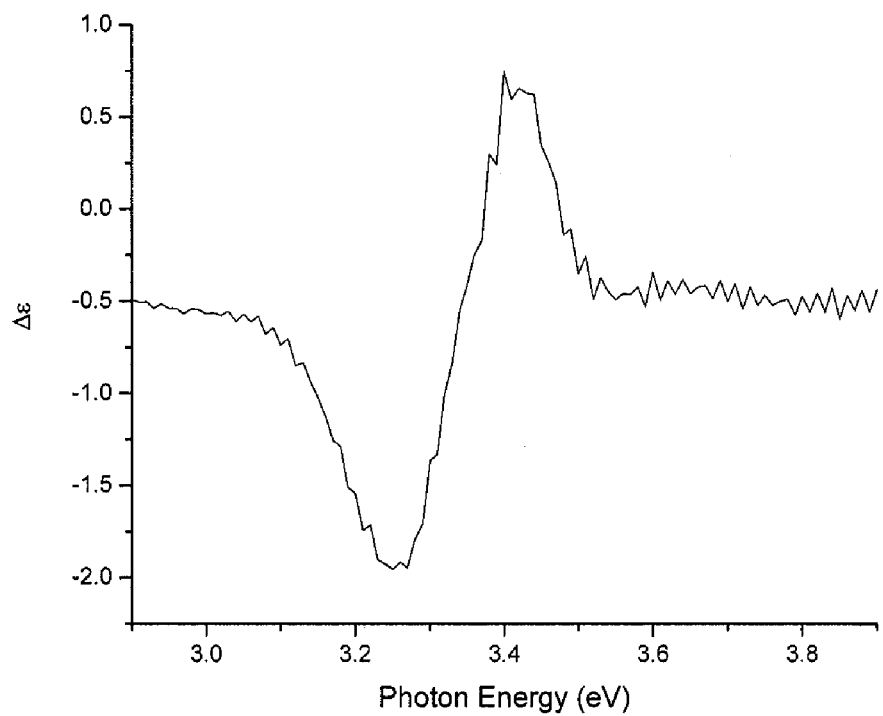
FIG. 6 is a graph showing the change in the imaginary part of the dielectric function for a silicon substrate subject to a uniform internal electric field, in accordance with embodiments of this disclosure.

In step 204, the result of step 202 may be subtracted from an unperturbed substrate dielectric function (See, e.g., FIG. 6). This may be accomplished using known tabular version of the optical constants for the unperturbed dielectric function. Alternatively, the unperturbed dielectric function may be determined by measuring from another location on the sample where the dielectric has not been deposited. In some embodiments, a similar sample may be measured for its unperturbed dielectric function and that value may be used in step 204. In other embodiments, the sample may be measured prior to the deposition of a dielectric oxide, using for example, step 202.

In step 206, the characteristics of the line shapes (e.g., the amplitude, period of oscillations) determined in step 204 may be analyzed to determine if it resembles a low or high field regime. In one embodiment, if the electric field created by the charge traps is less than the energy associated with the lifetime broadening of the substrates direct absorption edge, then one will see a graph similar to FIG. 1. However, if the induced electric field is appreciably high such that the band structure of the substrate has changed and the field is comparable (e.g., greater than or equal) to the band edge energy of the substrate, Franz-Keldysh oscillations in the data found in step 204 may be observed.

Figure 7:
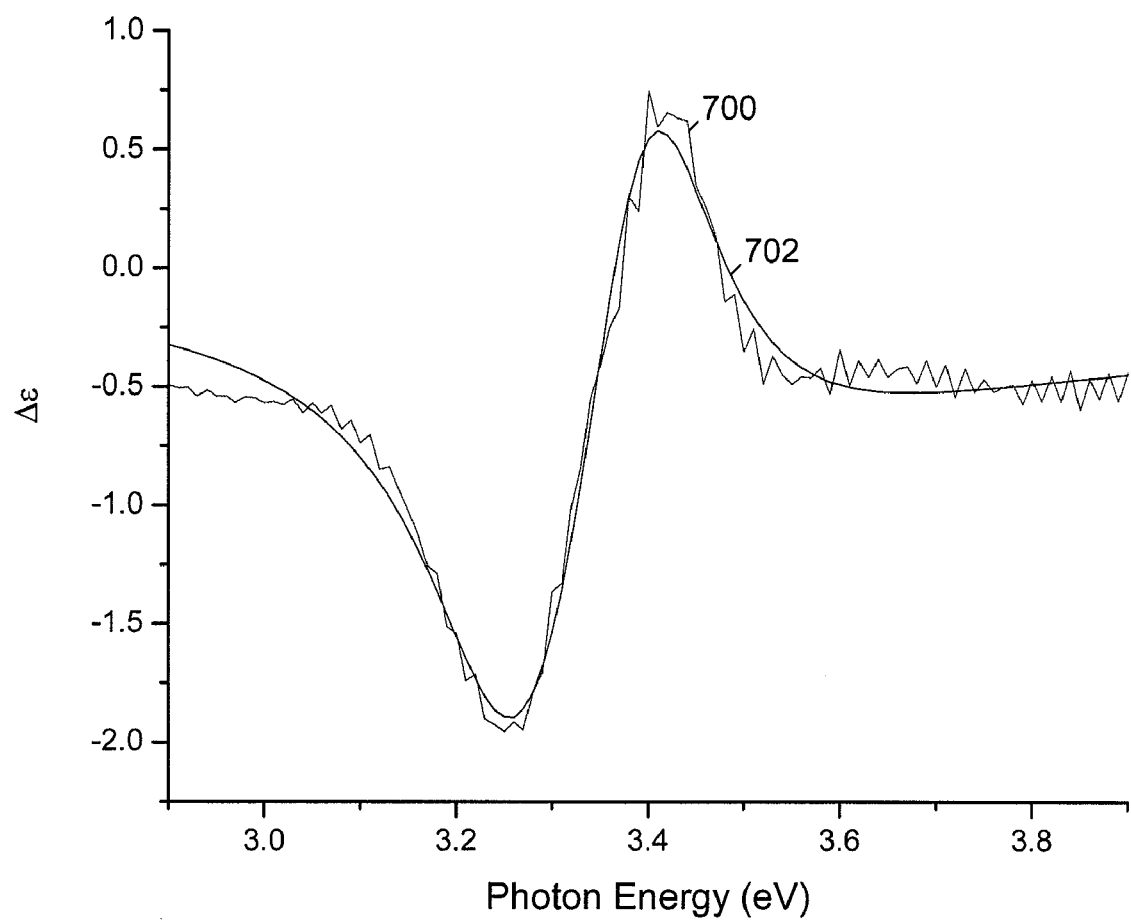
FIG. 7 is a graph showing the derivative functional form fit to the data shown in FIG. 6 using a least square regression technique, in accordance with embodiments of this disclosure.

In step 208, a functional form line shape may be applied to $\Delta\in$ from step 202, as shown in FIG. 7. For example, a functional form line shape may be applied data line 700 resulting in line 702. In one respect, a third derivative functional form Lorentzian line shape to obtained $\Delta\in$, using, for example, the following equation:

$$\text{Re}\left[\frac{Ce^{i\theta}}{(E-E_g+i\Gamma)^n}\right] \qquad \text{Eq. 5}$$

where C and θ are amplitude and phase factors that vary slowly with energy, E. $E_g$ corresponds with the inversion origin of the line shape, which is the E1 critical point (i.e. fundamental absorption edge) for this case. $\Gamma$ is the broadening, and n is the dimensionality of the line shape.

In step 210, the amplitude of the line shape fit of step 208 may be determined. In one embodiment, the amplitude of the line shape may be determined by performing a least square regression fit on Eq. 5. The parameter C, is the amplitude, and represents the height of the derivative line shape. Next, the square root of the amplitude may be determined, where the square root of the amplitude scales as the electric field (step 212). See Eq. 1.

The scalar potential in the space charge region may be determined, where the scalar potential is defined as the integral along the electric field path, integrated with respect to the unit of length (step 214). For a homogenous field transverse to the sample surface, this integral reduces to:

$$V=Ed, \qquad \text{Eq. 6}$$

where d is the interfacial layer region thickness obtained in step 202. The charge trap density may subsequently be obtained using Poisson's equation (Eq. 2 or Eq. 3) with knowledge of the scalar potential.

EXAMPLES

The following examples are included to demonstrate specific embodiments of this disclosure. It should be appreciated by those of ordinary skill in the art that the techniques disclosed in the examples that follow represent techniques discovered by the inventor to function well in the practice of the invention, and thus can be considered to constitute specific modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

A first sample with substantially less charge trap density at the interface (e.g., HF cleaned silicon surface without a HfO2 film with a typical charge trap density of about $1\times10^{10}$ cm$^{-2}$ to $5\times10^{10}$ cm$^{-2}$) and a second sample with an expected high density of charge traps at the interface are tested using techniques of the present disclosure (e.g., using the steps described in FIG. 2). In particular, the first sample includes a (100)-oriented silicon surface (HF cleaned surface) having about 1.4 nanometers silicon dioxide ($SiO_2$) layer. The second sample with the expected high density of charge traps includes a (100) silicon surface (HF cleaned surface) with an atomic layer deposited $HfO_2$ layer having a thickness of about 3 nm and a typical charge trap density values of about $1\times10^{11}$ cm$^{-2}$ to $5\times10^{11}$ cm$^{-2}$.

Figure 8:
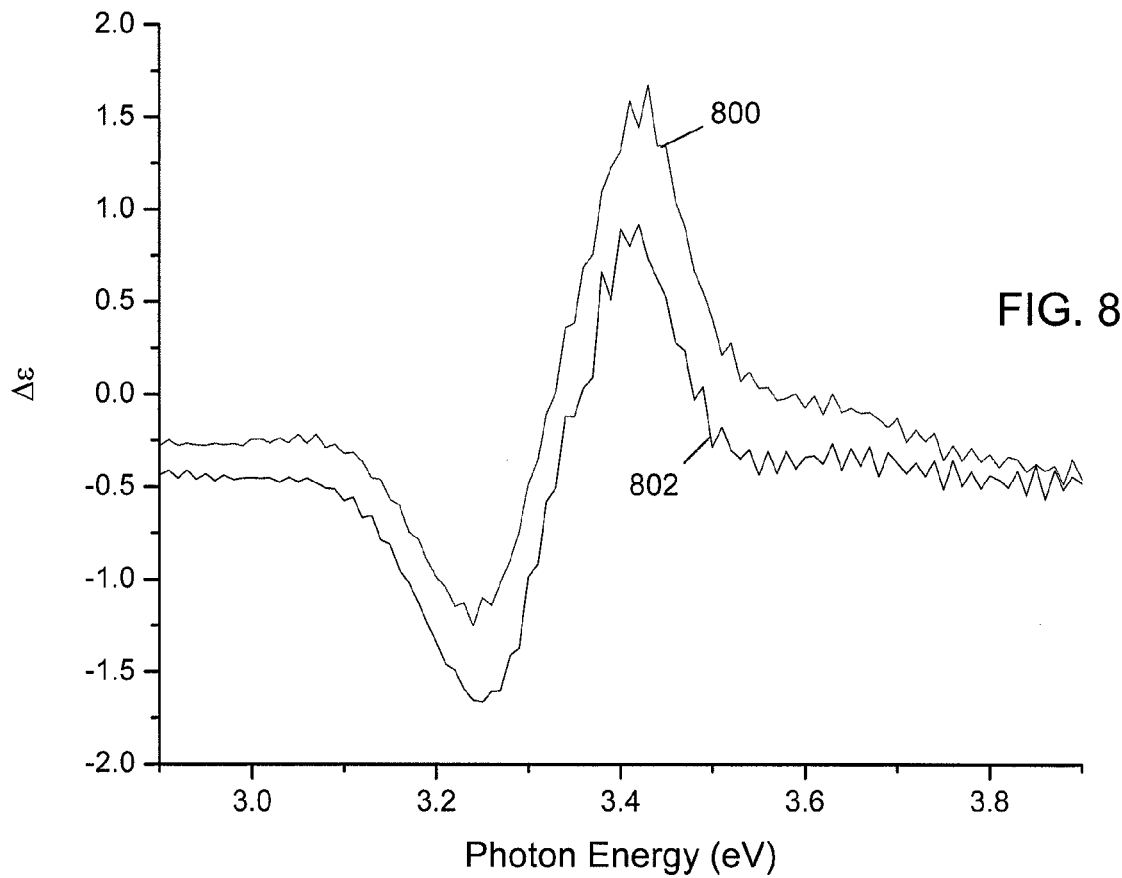
FIG. 8 is a graph showing a change in a dielectric function for two samples, in accordance with embodiments of this disclosure.

Referring to FIG. 8, the amplitude of the silicon sample with the $HfO_2$ layer (800) is about twice much as the silicon sample with silicon dioxide (802), as expected due to the a higher charge trap density for $HfO_2$ films compared to the HF cleaned silicon sample.

Also shown in FIG. 8 is the silicon direct absorption edge for both the $HfO_2$ sample (800) and the silicon dioxide sample (802) at an energy of about 3.375 electron volts (eV). If strain or other phenomena were present that may shift the direct absorption edge of silicon, then the peak energies may be different, but could also lead to graphs similar to what is shown in FIG. 8. In some respects, when the direct absorption edge for each sample is substantially similar, the only mechanism for changing the critical point is known and understood by those of ordinary skill in the art to be that due to electric field perturbations of the dielectric function (e.g., typical of low field modulation).

Example 2

This example provides a correlation to second harmonic generation (SHG) results. First, five (100) silicon substrates were prepared with an initial HF last treatment followed by growth of the $SiO_2$ interlayer using ozonated ($O_3$) water (HCl 0.2%) using techniques known in the art. Following the surface clean, a 45% silicate (HfSiO) gate dielectric was deposited via atomic layer deposition (ALD) on each wafer. One wafer (wafer 900 of FIG. 9) was left as-deposited and received no further post deposition anneals, while the remaining four wafers were annealed in an $NH_3$ ambient at 600° C. (wafer 902), 700° C. (wafer 904), 800° C. (wafer 906), and 900° C. (wafer 908). Spectroscopic ellipsometry data was taken on a J.A. Woollam Co. ellipsometer over the spectroscopic range of 0.75 eV –5.0 eV by 0.02 eV increments and an angle of incidence of 70-78 degrees by 4 degree increments.

Figure 9:
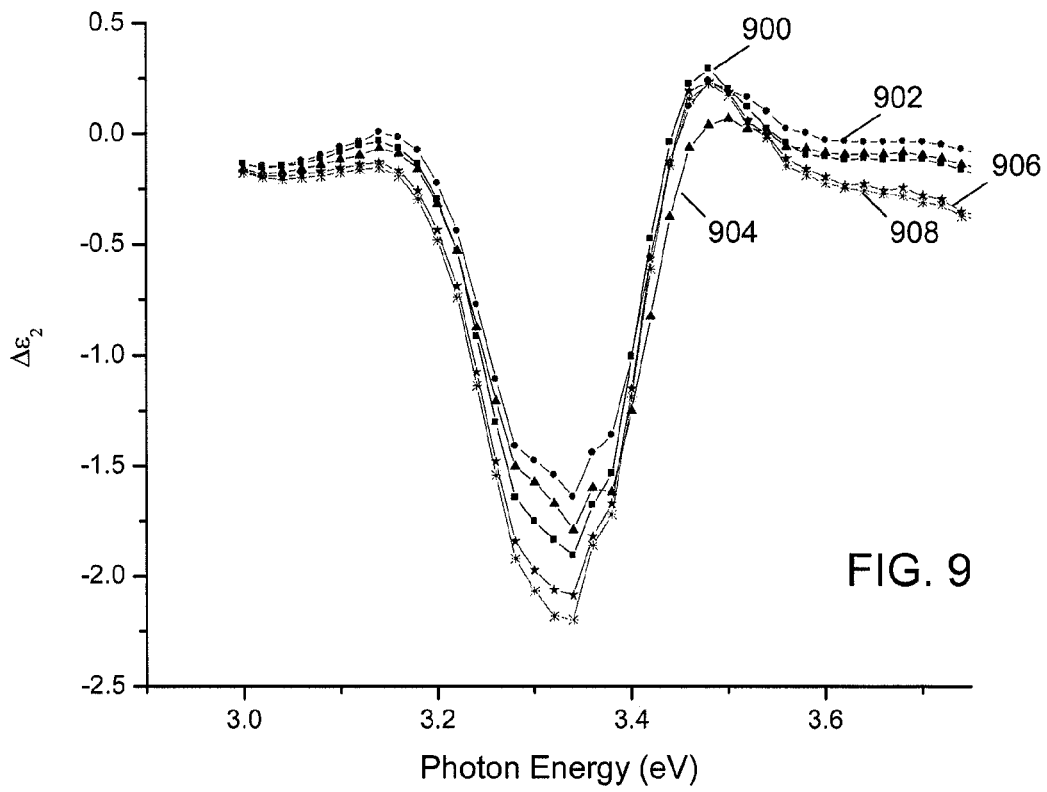
FIG. 9 is a graph showing a change in dielectric functions for different samples, in accordance with embodiments of this disclosure.
Figure 10:
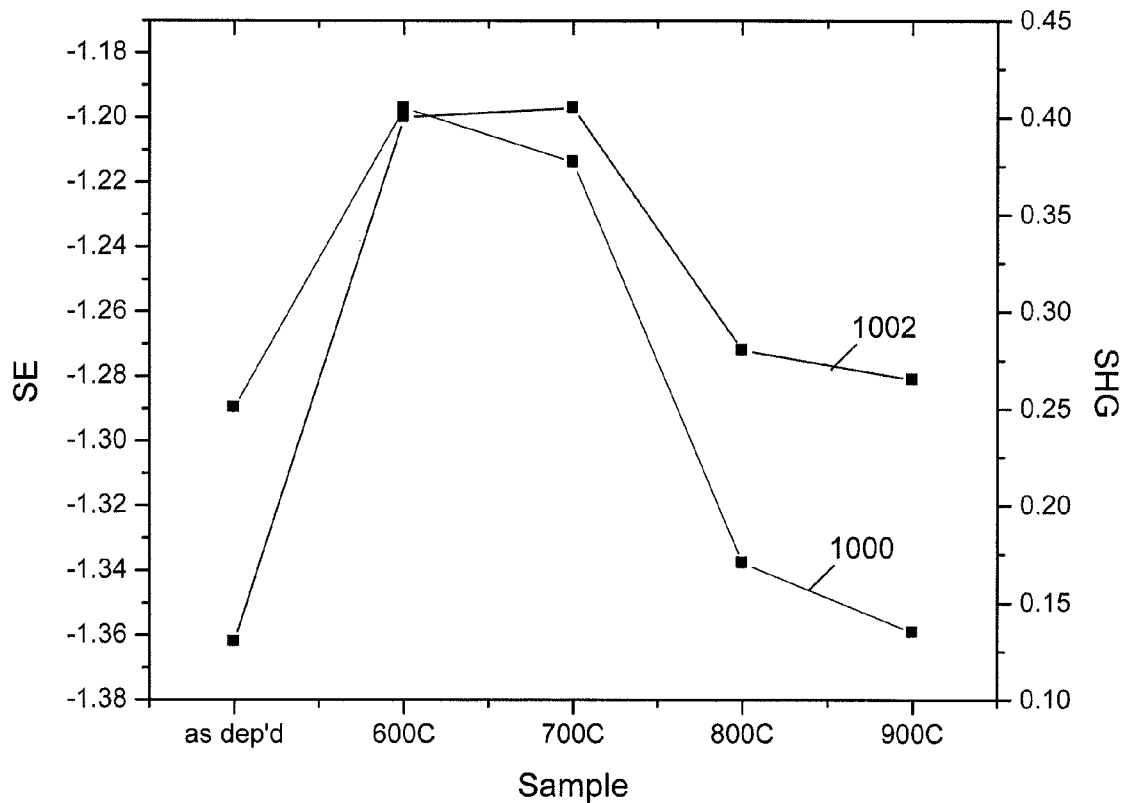
FIG. 10 is a graph comparing spectroscopic ellipsometry results and second harmonic generation results, in accordance with embodiments of this disclosure.

The method of the present disclosure, for example, the method outlined in FIG. 2 was performed on each of the five samples (900, 902, 904, 906, and 908) and the change in the imaginary part of the dielectric function ($\Delta\in_2$) of each sample is shown in FIG. 9. As may be seen, the line shape is invariant with respect to the annealing conditions, but the amplitude of the change in the substrate dielectric function appears to change with anneal temperature. Eq. 3 was therefore fit to each line shape below to extract the amplitude, C. FIG. 10 shows the SE results (1000) along with data from the SHG (1002). In particular, the SHG was taken on each of these five wafers and showed similar sensitivity to the annealing conditions as the SE results.

In some respects, the change in both the SE and SHG response may be due to a large DC electric field being created by thermally assisted electrons from the substrate being injected into the oxygen vacancies located at the substrate/HfSiO interface for temperatures between about 500° C.-700° C. For temperatures greater than 700° C., thermally assisted hole injection may possibly compete with electron injection and compensates the trapped negative charge, ultimately lowering the strength of the internal DC electric field.

Example 3

The following example shows a correlation between electrical results indicating sensitivity and identifying charge traps. The samples include three gate dielectrics ($HfO_2$, HfTiO, and HfTaTiO) formed by oxidizing the physical vapor deposition (PVD) metals (Hf, Ti, and Ta, respectively) with post-deposition anneals (PDAs). Each of the three gate dielectric was formed on a separate 8-inch, (100) silicon surface treated with hydrofluoric acid ("HF-Last"). After the metal deposition, a portion of each wafer was subsequently annealed (PDA) at 900° C. for 30 seconds in a $N_2$ ambient for the SE measurement. These samples were measured using a J. A. Woollam spectroscopic ellipsometer. In particular, the measurements were taken at two angles of incidence, 70° and 76°, across a 0.75-6.55 eV spectroscopic range with a scanning step size of 0.05 eV.

The electrical measurements were performed in which the gate is tied to a pulse generator, the substrate grounded, and the source and drain are coupled together and reversed biased. Basic charge pumping involves sweeping the base of a gate pulse train from a low accumulation level to a high inversion level. A DC current is then measured at the substrate. The peak current occurs when the base level is lower than the flat band voltage and the top level is greater than the threshold voltage. This peak current is proportional to the electrically active defect densities in the dielectric material at or near the semiconductor interface.

Figure 11:
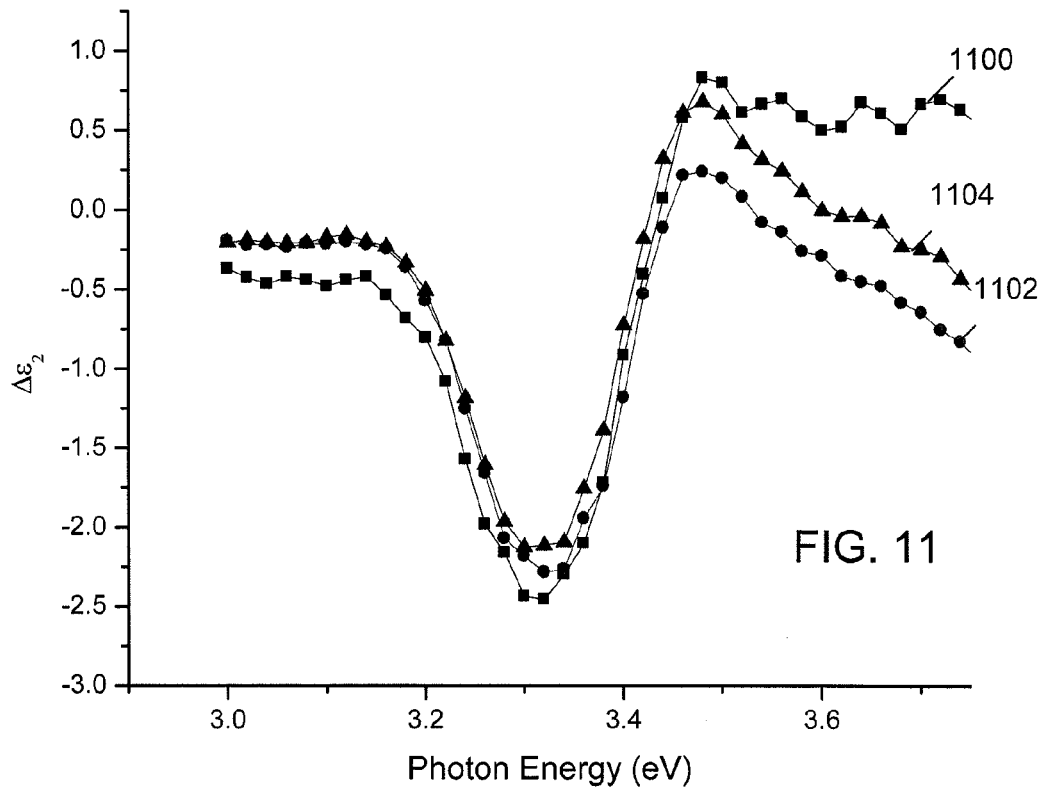
FIG. 11 is a graph showing imaginary parts of a change of dielectric functions for different samples, in accordance with embodiments of this disclosure.

Referring to FIG. 11, the change in the imaginary part of the dielectric function ($\Delta\varepsilon_2$) for the samples is illustrated. The amplitude of each peak (corresponding to the internal electric field) appears to consistently decrease from the $HfO_2$ sample (1100), to the HfTiO sample (1102), followed by the HfTaTiO sample (1104). The amplitude was obtained by fitting Eq. 3 to each line shape in FIG. 4. The amplitude is subsequently plotted versus the hysterisis observed in the flat band voltage (shown in FIG. 12A), where the amplitude appears to scale linearly with the electrical measurement.

Figures 12A, 12B:
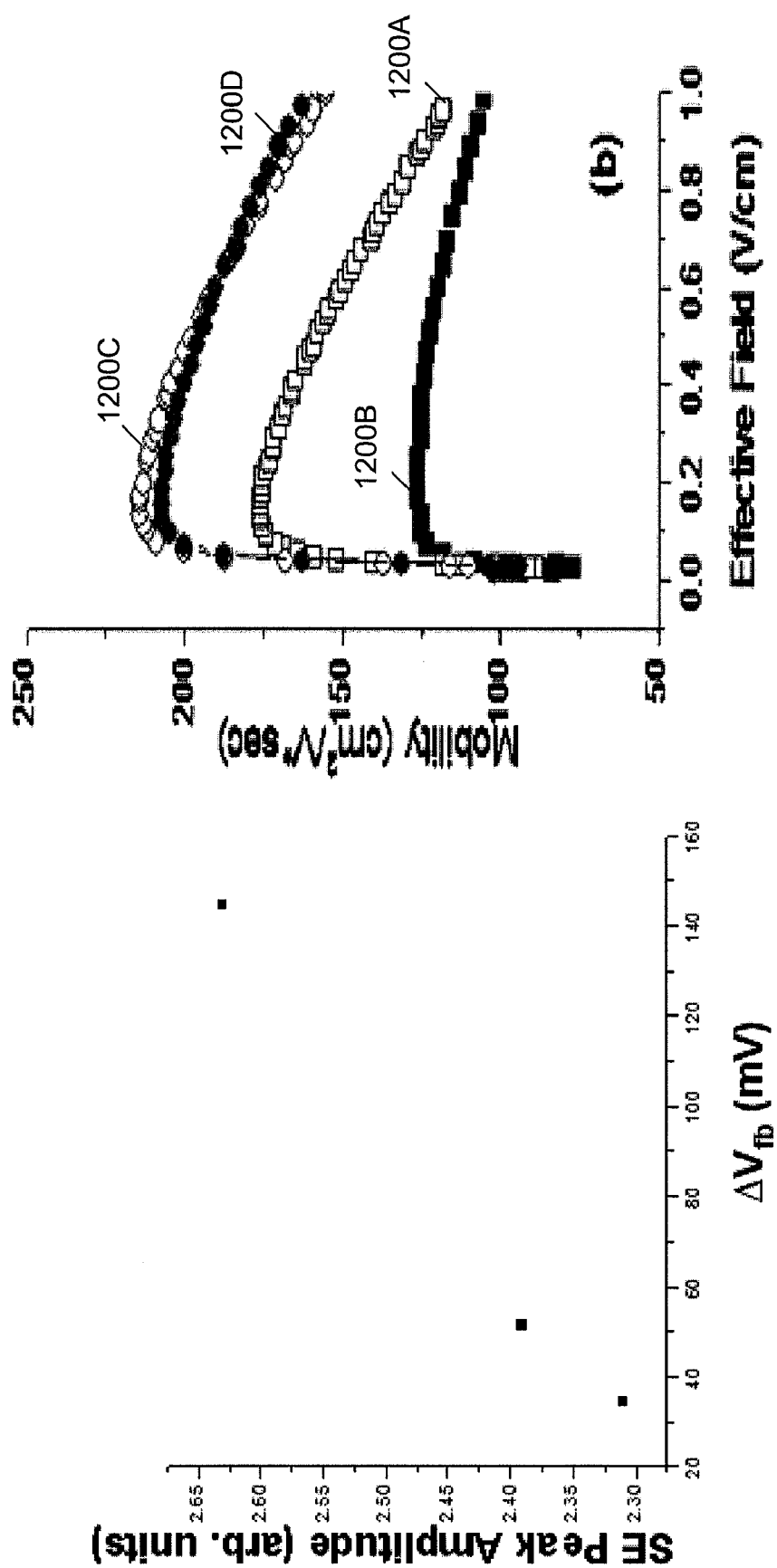
FIG. 12A is a graph showing a peak amplitude in correlation to the change in a flat band voltage ($V_{fb}$), in accordance with embodiments of this disclosure.
FIG. 12B is a graph comparing DC and AC mobilities for different samples, in accordance with embodiments of this disclosure.

Next, electrical measurements were performed on capacitors and transistors made from some of the wafers to determine their charge trapping characteristics. In particular, single pulse measurements were done and the mobility extracted from the pulsed drain current-gate voltage ($I_d$-$V_g$) using, for example, an electron probe was compared to mobility from DC $I_d$-$V_g$ values to determine charge trapping characteristics (as shown in FIG. 12B). The greater difference between the DC and AC mobilities values from the $HfO_2$ sample (1200A and 1200B, respectively) indicates that $HfO_2$ has more shallow traps as compared to that of the AC and DC mobilities of HfTaTiO (1200C and 1200D, respectively).

All of the methods disclosed and claimed can be made and executed without undue experimentation in light of the present disclosure. While the methods of this invention have been described in terms of embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope, and concept of the disclosure as defined by the appended claims.

The invention claimed is:

1. A method comprising:
   providing a semiconductor material comprising a semiconductor substrate and a dielectric layer;
   obtaining spectroscopic data corresponding to a region of interest that coincides with a direct absorption edge of the semiconductor substrate;
   determining a perturbed substrate dielectric function using the spectroscopic data without applying an external electric field to the semiconductor material;
   determining an amplitude of a dielectric function change using the perturbed substrate dielectric function and an unperturbed substrate dielectric function;
   determining an electric field of a space charge region of the semiconductor material using the amplitude of the dielectric function change; and
   determining a charge trap density of an interface between the semiconductor substrate and the dielectric layer using the electric field of the space charge region.

2. The method of claim 1, the semiconductor substrate comprising a crystalline material.

3. The method of claim 2, the crystalline material being selected from the group consisting of silicon, germanium, gallium arsenide (GaAs), gallium nitride (GaN), indium phosphide (InP), zinc sulfide (ZnS), silicon germanium (SiGe), Silicon-on-Insulator (SOI), and silicon germanium-on-Insulator (GeOI).

4. The method of claim 1, the dielectric layer being selected from the group consisting of silicon dioxide, silicon oxynitride, hafnium dioxide, hafnium silicates, hafnium silicon nitrides, zirconium oxides, zirconium silicates, and zirconium silicon nitrides.

5. The method of claim 1, the step of obtaining spectroscopic data comprising determining Psi, Del, or reflectivity spectroscopic data.

6. The method of claim 1, the step of determining an amplitude comprising performing a least square regression fit.

7. The method of claim 1, the step of determining charge trap density comprising using Poisson's equation.

8. A system comprising:
   a light source for illuminating a semiconductor material comprising a semiconductor substrate and a dielectric oxide layer;
   a detector configured for detecting light reflected from the semiconductor material; and
   a processor coupled to the detector, the processor configured for:
      obtaining spectroscopic data corresponding to a region of interest that coincides with a direct absorption edge of the semiconductor substrate;
      determining a perturbed substrate dielectric function using the spectroscopic data without applying an external electric field to the semiconductor material;
      determining an amplitude of a dielectric function change using the perturbed substrate dielectric function and an unperturbed substrate dielectric function;
      determining an electric field of a space charge region of the semiconductor material using the amplitude of the dielectric function change; and
      determining a charge trap density of an interface between the semiconductor substrate and the dielectric layer using the electric field of the space charge region.

9. The system of claim 8, the semiconductor substrate comprising a crystalline material.

10. The system of claim 9, the crystalline material being selected from the group consisting of silicon, germanium, gallium arsenide (GaAs), gallium nitride (GaN), indium phosphide (InP), zinc sulfide (ZnS), silicon germanium (SiGe), Silicon-on-Insulator (SOI), and silicon germanium-on-Insulator (GeOI).

11. A method comprising:
providing a semiconductor material;
obtaining spectroscopic data corresponding to a region of interest that coincides with a direct absorption edge of the semiconductor substrate; and
determining a perturbed substrate dielectric function using the spectroscopic data without applying an external electric field to the semiconductor material.

12. The method of claim 11, the step of obtaining spectroscopic data comprising obtaining Psi, Del, or reflectivity spectroscopic data.

13. The method of claim 11, further comprising determining an electric field of the semiconductor material as a function of the perturbed substrate dielectric function.

14. The method of claim 13, further comprising determining a charge trap density between the semiconductor material and a dielectric layer as a function of the electric field without applying an external electric field to the semiconductor material.

15. A method comprising:
providing a semiconductor material comprising a semiconductor substrate and a dielectric layer;
determining a perturbed substrate dielectric function using the spectroscopic data without applying an external electric field to the semiconductor material;
determining an electric field by using the perturbed substrate dielectric function; and
determining a charge trap density between the semiconductor substrate and the dielectric layer using the electric field.

16. The method of claim 15, the step of determining a perturbed substrate dielectric function comprising obtaining spectroscopic data from a region of interest that coincides with a direct absorption edge of the semiconductor substrate.

17. The method of claim 16, the step of obtaining spectroscopic data comprising obtaining Psi, Del, or reflectivity spectroscopic data.

* * * * *

UNITED STATES PATENT AND TRADEMARK OFFICE
CERTIFICATE OF CORRECTION

PATENT NO.       : 7,595,204 B2                                    Page 1 of 1
APPLICATION NO.  : 11/464884
DATED            : September 29, 2009
INVENTOR(S)      : James Martin Price It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this

Twenty-eighth Day of September, 2010

David J. Kappos
*Director of the United States Patent and Trademark Office*